United States Patent [19]

Shiota et al.

[11] Patent Number: 4,540,825

[45] Date of Patent: Sep. 10, 1985

[54] METHOD FOR PRODUCING 2-CYCLOPENTENONES

[75] Inventors: Katsuyuki Shiota, Toyonaka; Kunihiko Tanaka, Nara; Masayoshi Minai, Moriyama, all of Japan

[73] Assignee: Sumitomo Chemical Company, Limited, Osaka, Japan

[21] Appl. No.: 595,681

[22] Filed: Apr. 2, 1984

[30] Foreign Application Priority Data

Apr. 19, 1983 [JP] Japan .................................. 58-69566

[51] Int. Cl.³ .............................................. C07C 45/67
[52] U.S. Cl. ...................................... 568/341; 568/310
[58] Field of Search ........................ 568/341, 310, 361

[56] References Cited

U.S. PATENT DOCUMENTS

| | | | |
|---|---|---|---|
| 4,329,508 | 5/1982 | Ho et al. | 568/361 |
| 4,347,386 | 8/1982 | Saito et al. | 568/341 |
| 4,371,711 | 2/1983 | Saito et al. | 568/341 |

OTHER PUBLICATIONS

Fieser et al., "Reagents for Organic Synthesis, vol. 4, pp. 17–19, (1978).

*Primary Examiner*—James H. Reamer
*Attorney, Agent, or Firm*—Stevens, Davis, Miller & Mosher

[57] ABSTRACT

A method for producing 2-cyclopentenones represented by the formula,

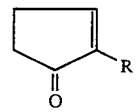

wherein R represents an alkyl, alkenyl, cycloalkyl, substituted or non-substituted aryl or aralkyl group, which comprises heating 4-cyclopentenones represented by the formula,

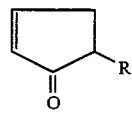

wherein R has the same meaning as above, in the presence of 1,8-diaza-bicyclo[5,4,0]undecene or its organic acid salt.

The 2-cyclopentenones are useful as an intermediate for perfumes, medicines and agricultural chemicals.

2 Claims, No Drawings

METHOD FOR PRODUCING 2-CYCLOPENTENONES

The present invention relates to a method for producing 2-cyclopentenones represented by the formula (I),

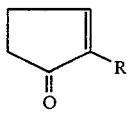
(I)

wherein R represents an alkyl, alkenyl, cycloalkyl, substituted or non-substituted aryl or aralkyl group, by the rearrangement of 4-cyclopentenones represented by the formula (II),

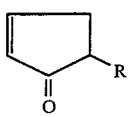
(II)

wherein R has the same meaning as above.

2-Cyclopentenones represented by the formula (I) are a useful compound as an intermediate for jasmonate and jasmone which are a perfume and prostaglandins which are a medicine as well as for agricultural chemicals.

The conventionally well-known methods for producing these 2-cyclopentenones include the rearrangement of 4-cyclopentenones with an alkali such as KOH or Lewis acid such as $BF_3$ as catalyst [Tetrahedron, 39–40, 1979; Japanese Patent Application Kokai (Laid-open) No. 56431/1976], the rearrangement thereof by heating to 250° to 300° C. without a catalyst, and the like. Either of these methods, however, has a defect that the yield is insufficient and besides large amounts of by-product are produced, so that they are not satisfactory as an industrial method.

For this reason, the present inventors extensively studied a method for producing 2-cyclopentenones advantageously by rearranging 4-cyclopentenones in a high yield and easily in industry, and as a result, found that excellent effect can be obtained when the rearrangement is carried out with a specified compound as catalyst. The present inventors thus attained to the present invention.

According to the present invention, there is provided a method for producing 2-cyclopentenones represented by the foregoing formula (I) characterized in that 4-cyclopentenones represented by the foregoing formula (II) is rearranged by heating in the presence of 1,8-diazabicyclo[5,4,0]undecene (hereinafter referred to as DBU) or its organic acid salt.

4-Cyclopentenones used as a material in the present invention are easily produced by using, for example, furancarbinols as material [Japanese Patent Application Kokai (Laid-open) No. 95935/1982].

In this method, 4-cyclopentenones are sometimes obtained as a mixture with 2-cyclopentenones which are an objective compound of the present invention. In the present invention, however, 4-cyclopentenones, which are a material, need not always be a simple substance, but they may be a mixture of cyclopentenones containing 2-cyclopentenones in any proportion.

The following compounds are given as such 4-cyclopentenones, and they are converted to 2-cyclopentenones by the shift of the double bond from 4-position to 2-position through the rearrangement of the present invention: 2-Methyl-4-cyclopentenone, 2-ethyl-4-cyclopentenone, 2-n-propyl-4-cyclopentenone, 2-isopropyl-4-cyclopentenone, 2-n-butyl-4-cyclopentenone, 2-isobutyl-4-cyclopentenone, 2-n-pentyl-4-cyclopentenone, 2-isopentyl-4-cyclopentenone, 2-n-hexyl-4-cyclopentenone, 2-n-heptyl-4-cyclopentenone, 2-allyl-4-cyclopentenone, 2-(2-cis-butenyl)-4-cyclopentenone, 2-(2-cis-pentenyl)-4-cyclopentenone, 2-(2-trans-pentenyl)-4-cyclopentenone, 2-(3-cis-hexenyl)-4-cyclopentenone, 2-cyclopentyl-4-cyclopentenone, 2-cyclohexyl-4-cyclopentenone, 2-cycloheptyl-4-cyclopentenone, 2-phenyl-4-cyclopentenone, 2-tolyl-4-cyclopentenone and 2-benzyl-4-cyclopentenone.

In the rearrangement of the present invention, DBU or its organic acid salt is used as catalyst, and the amount of the catalyst used is generally 0.0005 to 10 times by weight, preferably 0.001 to 5 times by weight based on 4-cyclopentenones or a mixture of cyclopentenones.

When DBU is used in the form of an organic acid salt, the organic acid includes for example aromatic compounds having an OH group such as phenol, cresol, etc., and fatty acids such as oleic acid, octylic acid, etc.

This reaction can be carried out without a solvent, but a solvent may be used as need arises.

As such solvent, there are given solvents which are inert to this reaction, for example, water and alcohols, ethers, ketones and aliphatic, aromatic or halogenated hydrocarbons such as methanol, ethanol, isopropyl alcohol, ethylene glycol, diethyl ether, tetrahydrofuran, dioxane, methyl isobutyl ketone, DMF, DMSO, benzene, toluene, chloroform, dichloromethane and the like. These solvents may be used alone or in combination.

When the solvent is used, its amount used is not particularly limited, but generally, it is 1 to 20 times by weight based on 4-cyclopentenones or a mixture of cyclopentenones.

The reaction temperature is generally 20° to 220° C., preferably 50° to 200° C.

Thus, according to the method of the present invention, 2-cyclopentenones can be obtained in a high yield and easily. Besides, another advantage of the method of the present invention is that, in the production of jasmonate using 2-cyclopentenones as material, the reaction solution obtained by the method of the present invention can be used as such as a material for said production without removing DBU therefrom. This may be said to be very advantageous, considering that, when 2-cyclopentenones have been produced using an alkali or Lewis acid as catalyst according to the conventional methods, the catalyst must be removed from the reaction solution obtained.

Next, the present invention will be illustrated with reference to the following examples. In the examples, all parts are by weight.

EXAMPLE 1

To a four-necked flask equipped with a stirrer, thermometer and condenser were added 4 parts of 2-pentyl-4-cyclopentenone, 16 parts of toluene and 2 parts of DBU, and the mixture was stirred under reflux for 2 hours in a nitrogen stream. Quantitative analysis by gas chromatography showed that 3.96 parts of 2-pentyl-2-cyclopentenone was obtained. The isomerization yield was 99.0%.

EXAMPLE 2

Four parts of 2-pentyl-4-cyclopentenone and 0.04 part of DBU were added to the same apparatus as used in Example 1 and stirred at 150° C. for 2 hours in a nitrogen stream. Quantitative analysis by gas chromatography showed that 3.94 parts of 2-pentyl-2-cyclopentenone was obtained. The isomerization yield was 98.5%.

EXAMPLE 3

Four parts of 2-pentyl-4-cyclopentenone and 0.04 part of DBU were added to the same apparatus as used in Example 1 and stirred at 120° C. for 7 hours in a nitrogen stream. Quantitative analysis by gas chromatography showed that 3.92 parts of 2-pentyl-2-cyclopentenone was obtained. The isomerization yield was 98.0%.

EXAMPLE 4

To the same apparatus as used in Example 1 were added 4 parts of a mixture of 2-pentyl-4-cyclopentenone (A) and 2-pentyl-2-cyclopentenone (B) [weight ratio of (A) to (B)=20 to 80] and 0.04 part of DBU, and the mixture was stirred at 120° C. for 4 hours in a nitrogen stream. Quantitative analysis by gas chromatography showed that 3.96 parts of 2-pentyl-2-cyclopentenone was obtained. The isomerization yield was 99.0% based on (A)+(B).

EXAMPLE 5

To the same apparatus as used in Example 1 were added 4 parts of a mixture of 2-pentyl-4-cyclopentenone (A) and 2-pentyl-2-cyclopentenone (B) [weight ratio of (A) to (B)=20 to 80] and 0.04 part of DBU-phenol salt, and the mixture was stirred at 120° C. for 6 hours in a nitrogen stream. Quantitative analysis by gas chromatography showed that 3.95 parts of 2-pentyl-2-cyclopentenone was obtained. The isomerization yield was 98.7% based on (A)+(B).

EXAMPLES 6 TO 12

Reaction was carried out using various 4-cyclopentenones according to Example 3. The results are shown in Table 1.

TABLE 1

| No. | Material (II) R | Catalyst Name | Amount used based on material | Reaction condition | Yield of 2-cyclopentenones |
|---|---|---|---|---|---|
| 6 | n-Pentyl | DBU-octylic acid salt | 1/100 | 120° C. × 8 hr | 97% |
| 7 | 2-Cis-pentenyl | DBU | " | 120° C. × 5 hr | 98% |
| 8 | Phenyl | DBU | " | 120° C. × 6 hr | 96% |
| 9 | Cyclohexyl | DBU-phenol salt | " | 120° C. × 6 hr | 98% |
| 10 | Allyl | DBU | " | 120° C. × 6 hr | 96% |
| 11 | n-Propyl | DBU | " | 120° C. × 6 hr | 98% |
| 12 | Benzyl | DBU | " | 120° C. × 7 hr | 95% |

COMPARATIVE EXAMPLE 1

To the same apparatus as used in Example 1 were added 4 parts of 2-pentyl-4-cyclopentenone, 40 parts of a 2.0% aqueous KOH solution and 20 parts of methanol, and the mixture was stirred under reflux for 6 hours in a nitrogen stream. After completion of the reaction, neutralization, extraction, separation and concentration were carried out. Quantitative analysis of the concentrated residue by gas chromatography showed that 3.02 parts of 2-pentyl-2-cyclopentenone was obtained. The isomerization yield was 75.5%.

What is claimed is:

1. A method for producing a 2-cyclopentenone represented by the formula,

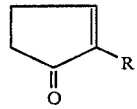

wherein R represents an alkyl, alkenyl or cycloalkyl group having 7 or less carbon atoms respectively, or a phenyl, tolyl or benzyl group, which comprises heating a 4-cyclopentenone represented by the formula,

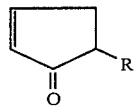

wherein R has the same meaning as above, in the presence of 1,8-diaza-bicyclo[5,4,0]undecene or its organic acid salt wherein the organic acid is phenol, cresol, oleic acid or octylic acid.

2. A method for producing 2-cyclopentenones according to claim 1, wherein the organic acid is phenol or octylic acid.

* * * * *